US007524405B2

(12) United States Patent
Sohn et al.

(10) Patent No.: US 7,524,405 B2
(45) Date of Patent: Apr. 28, 2009

(54) METHOD FOR SEPARATING OUT SOLVENT FROM A REACTION MIXTURE RESULTING FROM AN ISOCYANATE SYNTHESIS AND FOR PURIFYING THIS SOLVENT

(75) Inventors: Martin Sohn, Mannheim (DE); Eckhard Stroefer, Mannheim (DE); Filip Nevejans, St.Gillis-Waas (BE); Ulrich Penzel, Tettau (DE); Hans-Juergen Pallasch, Kallstadt (DE); Peter Van Den Abeel, Brasschaat (BE); Filip Deberdt, Muizen (BE); Jan D. Jacobs, Baton Rouge, LA (US); Wolfgang Mackenroth, Bad Duerkheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 700 days.

(21) Appl. No.: 10/539,610

(22) PCT Filed: Dec. 13, 2003

(86) PCT No.: PCT/EP03/14187

§ 371 (c)(1),
(2), (4) Date: Jun. 17, 2005

(87) PCT Pub. No.: WO2004/056761

PCT Pub. Date: Jul. 8, 2004

(65) Prior Publication Data

US 2006/0011463 A1 Jan. 19, 2006

(30) Foreign Application Priority Data

Dec. 19, 2002 (DE) ................................ 102 60 027

(51) Int. Cl.
*B01D 3/00* (2006.01)
*C07C 263/20* (2006.01)
(52) U.S. Cl. .................... 203/80; 203/27; 203/DIG. 8; 560/347; 560/352

(58) Field of Classification Search ...................... 203/2, 203/22, 25, 27, 80, DIG. 8; 560/347, 352
See application file for complete search history.

(56) References Cited

U.S. PATENT DOCUMENTS

| 2,884,359 | A | * | 4/1959 | Bloom et al. | .................. 203/52 |
| 3,410,888 | A | | 11/1968 | Hammond | |
| 3,658,656 | A | * | 4/1972 | Adica et al. | ................... 203/49 |
| 4,118,286 | A | * | 10/1978 | Burns et al. | ................... 203/89 |
| 4,195,032 | A | * | 3/1980 | Koster et al. | ................ 560/348 |
| 5,354,432 | A | * | 10/1994 | Arribas et al. | ................. 203/68 |
| 6,803,483 | B2 | * | 10/2004 | Lokum et al. | ............... 560/347 |
| 7,108,770 | B2 | * | 9/2006 | Grun et al. | .................... 203/29 |
| 2007/0265465 | A1 | * | 11/2007 | Keggenhoff et al. | ........ 560/347 |

FOREIGN PATENT DOCUMENTS

FR 1 399 472 5/1965

OTHER PUBLICATIONS

Ullmanns Encyklopaedie der technischen Chemie, vol. 7, (Polyurethane), 3. Edition, Carl Hanser Verlag, Muenchen-Wien, p. 76ff, 1993.
Von Werner Seifken, "Justus Liebigs Annalen Der Chemie" vol. 562, pp. 6-136, 1949.

* cited by examiner

*Primary Examiner*—Virginia Manoharan
(74) *Attorney, Agent, or Firm*—Oblon, Spivak, McClelland, Maier & Neustadt, P.C.

(57) ABSTRACT

The invention relates to a process for preparing isocyanates by reaction of amines with phosgene in the presence of inert organic solvents in a reactor and subsequent work-up of the reaction mixture leaving the reactor, wherein the solvent is separated off in a two-stage or multistage, preferably two-stage, distillation process in which the solvent is separated off at a pressure of 0.1-15 bar in a first apparatus and at 1-900 mbar in a second apparatus or further apparatuses, with the heat of condensation of the solvent vapor from the first apparatus being used for partial or complete vaporization of solvent in the second apparatus.

18 Claims, No Drawings

METHOD FOR SEPARATING OUT SOLVENT FROM A REACTION MIXTURE RESULTING FROM AN ISOCYANATE SYNTHESIS AND FOR PURIFYING THIS SOLVENT

The present invention relates to a process for separating off the solvent in the preparation of aromatic or aliphatic isocyanates.

Isocyanates have for a long time been produced in large quantities, particularly as starting materials for the preparation of polyurethanes. Among aromatic isocyanates, methylenedi(phenyl isocyanate) (MDI) and its higher homologues and tolylene diisocyanate (TDI) have the greatest industrial importance, while among aliphatic isocyanates, hexamethylene diisocyanate (HDI) and isophorone diisocyanate (IPDI) are most important.

The continuous preparation of organic isocyanates by reaction of primary organic amines with phosgene has been described many times and is carried out on a large industrial scale (cf., for example, Ullmanns Enzyklopädie der Technischen Chemie, Volume 7 (Polyurethane), 3rd revised edition, Carl Hanser Verlag, Munich-Vienna, p. 76ff (1993)).

The preparation of isocyanates from the corresponding amines by phosgenation is usually carried out in stirred vessels, in cascades of stirred vessels, in packed reaction columns or in unpacked columns. A mode of operation with recirculation is often necessary to achieve a sufficient residence time for complete reaction in a limited reaction volume (holdup). Since the reaction of amine and phosgene in the liquid phase is very fast, a mixing reactor is frequently used for the first reaction stage. Known mixing apparatuses include, in particular, nozzles such as annular slit nozzles, annular hole nozzles, smooth-jet mixing nozzles, fan-jet nozzles, angled jet chamber nozzles, three-fluid nozzles, countercurrent mixing chambers, Pitot tubes or Venturi mixing nozzles.

The first stage of the isocyanate synthesis is frequently carried out at a very low temperature and the second stage is then carried out at a significantly higher temperature in a residence apparatus (cold-hot phosgenation) (W. Siefken, Liebigs Analen der Chemie 562 (1949), page 96). A suspension of the intermediates carbamoyl chloride and amine hydrochloride is produced first at low temperature, in particular 0° C. or room temperature, at most 60° C., and this is then converted into the isocyanate at higher temperatures, in particular from 100 to 200° C., in a residence apparatus. Such two-stage processes are described, for example, in Ullmanns Enzyklopädie der Technischen Chemie, Volume 7 (Polyurethane), 3rd revised edition, Carl Hanser Verlag, Munich-Vienna, p. 76ff (1993).

To achieve high yields, the syntheses of isocyanates from amines and phosgene are generally carried out in organic solvents which are inert toward the starting materials and the end products. In a particular embodiment of the isocyanate synthesis, the isocyanate prepared in the process concerned can also be used as solvent, both for the amine and for the phosgene.

As inert organic solvents for the preparation of isocyanates, preference is given to using chlorinated aromatic hydrocarbons such as dichlorobenzene, chlorobenzene, trichlorobenzene or aromatic or aliphatic hydrocarbons such as toluene, xylene, benzene, pentane, hexane, heptane, octane, cyclohexane, biphenyl, ketones such as 2-butanone, methyl isobutyl ketone, esters such as diallyl isophthalate, ethyl acetate, butyl acetate, nitriles such as acetonitrile or sulfolane, etc.

After the reaction is complete, the solvent, which generally boils at a lower temperature than the isocyanate, is separated off from the isocyanate and any residue and is worked up by distillation. In the case of tolylene diisocyanate (TDI), this is followed by separation of the isocyanate from the residue by distillation and purification of the isocyanate by distillation or by crystallization. In addition, further separation operations can be carried out in order to separate the isomer mixture in the case of TDI and MDI or the oligomer mixture in the case of polymeric MDI into individual fractions having different isomer and oligomer compositions. TDI is generally in the form of a mixture of the two isomers 2,4-TDI and 2,6-TDI, generally as an 80:20 or 65:35 mixture.

The mixture of hydrogen chloride and phosgene obtained in the reaction of aliphatic or aromatic amines with phosgene to give the corresponding isocyanates can likewise contain more or less large amounts of solvent. This mixture is then generally separated into the usually gaseous hydrogen chloride and a generally liquid mixture of phosgene and possibly solvent. The phosgene or phosgene/solvent mixture is then recirculated to the reaction. A more or less large excess of phosgene is generally used, so that the phosgene used does not react completely with the amine despite high chemical yields of the amine/phosgene reaction in isocyanate production. The presence of solvent in this phosgene recycled stream generally causes no problems, but leads to dilution of the phosgene stream.

On the other hand, the isocyanate has to be completely separated off from the solvent which is recirculated to the reaction in order to rule out secondary reactions of the isocyanate with the amine.

U.S. Pat. No. 3,410,888 describes a process for isolating an aromatic diisocyanate which has two phenyl rings and in which the isocyanate groups are bound to carbon atoms of different phenyl rings from a reaction mixture. This applies to methylene-4,4'-,-2,4'- and -2,2'-di(phenyl isocyanate) (MDI) and mixtures of these isomers or polymethylenepolyphenylene polyisocyanate (PMDI). The process claimed comprises the process steps of firstly reacting an appropriate aromatic diamine with phosgene and subsequently separating off part of the resulting aromatic isocyanate by distillation in the solvent removal, secondly transferring the distillation residue (bottom product) to a second distillation apparatus over whose interior surface the residue is distributed as a thin film and whose temperature and pressure are sufficient to effect vaporization of the isocyanate, and thirdly taking off the vapor, which consists essentially of isocyanate, from this second distillation apparatus. The vapor is condensed and the isocyanate is stored. Possible apparatuses mentioned as distillation apparatus are climbing film evaporators, falling film evaporators and the like. The solvent in the isocyanate synthesis usually has a boiling point lower than that of the isocyanate; the boiling point is preferably at least 30° C. lower. In the case of a smaller boiling point difference, part of the isocyanate prepared can be separated off together with the solvent in the solvent removal. This is followed by the distillation of the crude isocyanate obtained as residue in a thin film evaporator. The partial removal of the isocyanate in the solvent removal has the advantage that undesirable intermediate boilers, e.g. colored impurities or components whose boiling point is between that of the isocyanate and that of the solvent, are also separated off in the solvent removal. The mixture of the isocyanate which has been partly separated off and the solvent is then recirculated as feed to the solvent removal or is passed to a separate evaporation or fractional distillation to concentrate the isocyanate. The latter is then recycled as feed to the solvent removal.

A disadvantage of this process is the fact that the isocyanate is partly separated off in the solvent removal, which makes additional purification of the solvent necessary.

It is an object of the present invention to develop a process for separating off the solvent, which allows complete separation of the isocyanate from the solvent and also gives energy savings.

We have found that this object is achieved by a two-stage or multistage, preferably two-stage, distillation process for separating off the solvent from a reaction product mixture from the isocyanate synthesis, in which the solvent separated off at from 0.1 to 15 bar, preferably from 0.5 to 3 bar, in a first apparatus, preferably a distillation column, and then at from 1 to 900 mbar, preferably from 100 to 500 mbar, in a second apparatus or further apparatuses, preferably likewise distillation columns, with the heat of condensation of the solvent vapor from the first apparatus being used for partial or complete vaporization of solvent in the second apparatus.

A process for preparing isocyanates by reaction of amines with phosgene in the presence of inert organic solvents in a reactor and subsequent work-up of the reaction mixture leaving the reactor, wherein the solvent is separated off in a two-stage or multistage, preferably two-stage, distillation process in which the solvent is separated off at a pressure of from 0.1 to 15 bar, preferably from 0.5 to 3 bar, in a first apparatus, preferably a distillation column, and at from 1 to 900 mbar, preferably from 50 to 500 mbar, in a second apparatus or further apparatuses, preferably likewise distillation columns, with the heat of condensation of the solvent vapor from the first apparatus being used for partial or complete vaporization of solvent in the second apparatus.

The temperature at the bottom of the first column is, depending on the pressure, in the range from 60° C. at 0.1 bar to 270° C. at 15 bar. The temperature at the bottom of the second column is, depending on the pressure, in the range from 75° C. at 1 mbar to 250° C. at 900 mbar.

In the first column, solvent vapor is separated off by distillation. The liquid fraction obtained as bottom product from this column is depressurized to the lower pressure level of the second apparatus either before or in the second apparatus and, in the former case, is fed into the second apparatus in which the remaining solvent is separated off. The transfer of the energy from the vapor from the first apparatus to the liquid phase of the second apparatus can be achieved using, in particular, a heat exchanger, for example a cross-flow apparatus, in which the condensing vapor effects vaporization of the liquid phase of the second apparatus, viz. the second column. The vapor and liquid phase can be conveyed in cocurrent or in countercurrent here. The vapor can be condensed in the jacket space or in the product space of the heat exchanger. It is not necessary to use a specific heat exchanger. It is possible to use any apparatus which makes a heat transfer surface available. The liquid of the second column can be taken off from the bottom, from a tray, from a liquid collector or from the feed line. The liquid is preferably taken from a tray or collector below the inlet of the second column. Both columns are preferably provided with an enrichment section. The second column can also be provided with a stripping section.

As internals, use is made of the known internals for distillation and rectification columns. For example, a tray column or a packed column can be used. Examples of trays are sieve trays, valve trays, bubble cap trays or dual-flow trays and examples of ordered packing are sheet metal packing, woven packing or mesh packing of all types. Ordered packing is particularly advantageous since it displays a low pressure drop. Beds of random packing elements are less suitable but are not ruled out in principle. Types of ordered packing which can be used are, for example, Sulzer BX, Sulzer CY, Sulzer Mellapak, Sulzer Mellapak Plus, Montz A3, Glitsch 4A, Kühni Rombopak and others. As bottom circulation vaporizer, it is in principle possible to use all types of vaporizer, with falling film evaporators or thin film evaporators being particularly advantageous because they enable vaporization which is gentle on the product to be achieved and they can also be operated at small temperature differences between the hot and cold sides. Thermal coupling can also be achieved in the form of intermediate vaporization on the second column. In the case of intermediate vaporization, the liquid is taken from an appropriate tray or collector of the column and passed to a heat exchanger. For energy reasons, it can be advantageous to precede the column used according to the present invention by a single-stage or multistage vaporization. In the case of preliminary vaporization, the liquid feed is fed into a vaporizer and partly or completely vaporized. The vapor stream and any remaining liquid stream is/are fed to the column. Both the preliminary vaporization and the intermediate vaporization can have one or more stages. As vaporizer, it is possible to use a flow-through vaporizer, preferably a falling film evaporator, long-tube evaporator or thin film evaporator. The condenser at the top can be located outside the column or be integrated into the column. It is possible to use both shell-and-tube apparatuses and plate apparatuses.

The process described can also have a multistage configuration, i.e. can use more than two columns. In this embodiment, the pressure is reduced before each successive apparatus to a level lower than that in the preceding apparatus and the energy of the vapor is used one or more times for partial or complete vaporization of the liquid phase of the subsequent apparatus. A process having more than 5 stages is no longer practical from the point of view of capital costs, but is not ruled out in principle.

To carry out the removal of solvent according to the present invention, preference is given, as indicated above, to using distillation columns. However, it is also possible to use single-stage apparatuses, for example flash apparatuses or evaporators.

In the process of the present invention, no isocyanate is taken off together with the solvent in the solvent removal. Instead, the objective of the distillation is a clean separation of the solvent from the isocyanate with minimization of the isocyanate content. If necessary, only low boilers are separated off in a further solvent purification stage.

This makes it possible to carry out complete separation of the solvent from the reaction mixture so that the solvent can be recirculated to the isocyanate production process without further work-up or additional purification. As a result of the vapor being used for vaporization of the reaction mixture, the process can be operated in an energetically advantageous fashion.

The process of the present invention can be used particularly advantageously for the work-up of the solvent in the preparation of TDI, MDI and HDI. As solvents in the preparation of TDI, MDI and HDI, it is possible to use chlorobenzene, dichlorobenzene or mixtures of the two or toluene.

The invention is illustrated by the following example.

EXAMPLE 6.14 kg/h of a reaction product mixture from the synthesis of tolylene diisocyanate (TDI) from toluenediamine (TDA) and phosgene were fed into the lower part of a distillation column having a diameter of 50 mm. The column is packed with 6 sections of mesh packing (Kühni Rombopak 9M, length of one section: 630 mm). The temperature at the bottom was 150° C., the pressure at the top was 1.3 bar abs. and the temperature at the top was 136° C. As bottom circulation vaporizer, use was made of a shell-and-tube apparatus containing 13 tubes. The composition of the feed (reaction product mixture from the isocyanate synthesis) was 5.1 kg/h (82% by weight) of chlorobenzene, 1.0 kg/h (16% by weight) of TDI including high-boiling TDI homologues, 0.01 kg/h (0.16% by weight) of $CCl_4$, 0.01 kg/h (0.16% by weight) of $CHCl_3$, 0.004 kg/h (0.06% by weight) of hydrogen chloride, small amounts of phosgene and chlorinated secondary components and also small amounts of low boilers. At the top of the first column, 2.7 kg/h of vapor were taken off and passed to a heat exchanger (cross-flow apparatus). In this heat exchanger, the feed to a second column was simultaneously preheated and partly vaporized by this vapor stream. The major part (1.7 kg/h) of the condensate of the vapor from the first column obtained in this heat exchanger was recirculated as recirculated solvent to the isocyanate synthesis and a smaller part of it (1.0 kg/h) was fed to the top of the first column as runback. At the bottom of the first column, 4.44 kg/h of liquid were taken off and fed to the abovementioned heat exchanger which was located in the feed line to the second column. The feed point was located in the middle part, i.e. between stripping section and enrichment section, of the second column. The second column likewise had a diameter of 50 mm and was packed with the same packing as the first column. The temperature at the bottom of this second column was 183° C., the pressure at the top was 120 mbar abs. and the temperature at the top was 68° C. As bottom circulation vaporizer, use was made of a shell-and-tube apparatus containing 13 tubes. 1.0 kg/h (97.6% by weight) of TDI including high-boiling TDI homologues, and 0.01 kg/h (1% by weight) of chlorinated secondary components were taken off at the bottom. This stream was subsequently passed to a distillation to produce pure TDI. 3.4 kg/h (99.3% by weight) of chlorobenzene, 0.01 kg/h (0.3% by weight) of $CCl_4$, 0.01 kg/h (0.3% by weight) of $CHCl_3$, 0.004 kg/h (0.1% by weight) of HCl and small amounts of phosgene and small amounts of other low boilers were obtained at the top of the second column. This stream was condensed and likewise recirculated as recirculated solvent to the reaction section of the TDI synthesis. Part of this stream was returned as runback to the top of the column.

We claim:

1. A process for preparing at least one isocyanate, comprising:
    reacting at least one amine with phosgene in the presence of at least one inert organic solvent in a reactor; and
    working up the reaction mixture leaving the reactor,
    wherein the at least one solvent is separated off from the at least one isocyanate in an at least a two-stage distillation process in which the at least one solvent is separated off at a pressure of from 0.1 to 15 bar in a first apparatus in the first stage and at from 1 to 900 mbar in a second apparatus in the second stage, wherein the heat of condensation of a solvent vapor from the first apparatus is utilized for vaporization of solvent in the second apparatus.

2. The process as claimed in claim 1, wherein distillation columns are used as the first apparatus and the second apparatus for separating off the solvent.

3. The process of claim 2, wherein the pressure in the first apparatus is from 0.5 to 3 bar.

4. The process of claim 2, wherein the pressure in the second apparatus is from 50 to 500 mbar.

5. The process of claim 2, wherein the heat of condensation of the solvent vapor from the first apparatus is utilized to vaporize the solvent of the second apparatus using a device.

6. The process of claim 5, wherein the device is selected from the group consisting of a flow-through vaporizer, a falling film evaporator, a long-tube evaporator, and a thin film evaporator.

7. The process of claim 2, wherein the at least one inert organic solvent is chlorobenzene, dichlorobenzene, toluene, or a combination of chlorobenzene and dichlorobenzene.

8. The process of claim 1, wherein the pressure in the first apparatus is from 0.5 to 3 bar.

9. The process of claim 8, wherein the pressure in the second apparatus is from 50 to 500 mbar.

10. The process of claim 8, wherein the heat of condensation of the solvent vapor from the first apparatus is utilized to vaporize the solvent of the second apparatus using a device.

11. The process of claim 10, wherein the device is selected from the group consisting of a flow-through vaporizer, a falling film evaporator, a long-tube evaporator, and a thin film evaporator.

12. The process of claim 8, wherein the at least one inert organic solvent is chlorobenzene, dichlorobenzene, toluene, or a combination of chlorobenzene and dichlorobenzene.

13. The process of claim 1, wherein the pressure in the second apparatus is from 50 to 500 mbar.

14. The process of claim 13, wherein the at least one inert organic solvent is chlorobenzene, dichlorobenzene, toluene, or a combination of chlorobenzene and dichlorobenzene.

15. The process of claim 1, wherein the heat of condensation of the solvent vapor from the first apparatus is utilized to vaporize the solvent of the second apparatus using a device.

16. The process of claim 15, wherein the device is selected from the group consisting of a flow-through vaporizer, a falling film evaporator, a long-tube evaporator, and a thin film evaporator.

17. The process of claim 1, wherein the at least one inert organic solvent is chlorobenzene, dichlorobenzene, toluene, or a combination of chlorobenzene and dichlorobenzene.

18. The process of claim 1, wherein the at least one isocyanate is tolylene diisocyanate, methylene-4,4'-di(phenyl isocyanate), methylene-2,4'-di(phenyl isocyanate), methylene-2,2'-di(phenyl isocyanate), polymethylenepolyphenylene polyisocyanate, hexamethylene diisocyanate, isophorone diisocyanate, or a mixture thereof.

* * * * *